United States Patent [19]

Cavazza et al.

[11] Patent Number: 5,494,924
[45] Date of Patent: Feb. 27, 1996

[54] THERAPEUTICAL METHOD FOR THE TREATMENT OF DERMATOSES USING O-ESTERS OF L-CARNITINE

[75] Inventors: Claudio Cavazza; Paolo Cavazza, both of Rome, Italy

[73] Assignee: Avantgarde S.p.A., Rome, Italy

[21] Appl. No.: 250,686

[22] Filed: May 27, 1994

[30] Foreign Application Priority Data

May 28, 1993 [IT] Italy .................. RM93A0356

[51] Int. Cl.⁶ .............. A61K 31/44; A61K 31/225; A61K 31/205
[52] U.S. Cl. .................. 514/357; 514/547; 514/556; 514/859; 514/863
[58] Field of Search ................. 514/357, 547, 514/556, 859, 863

[56] References Cited

U.S. PATENT DOCUMENTS

| | | | |
|---|---|---|---|
| 4,401,827 | 8/1983 | de Witt | 560/1 |
| 4,439,438 | 3/1984 | Cavazza | 514/357 |

*Primary Examiner*—Raymond Henley, III
*Assistant Examiner*—Kevin E. Weddington
*Attorney, Agent, or Firm*—Oblon, Spivak, McClelland, Maier & Neustadt

[57] ABSTRACT

The use of O-esters of L-carnitine with saturated bicarboxylic acids (e.g. azelaic, sebacic, suberic and pimelic acid) or unsaturated monocarboxylic acids (e.g. linoleic, linolenic, oleic and orachidonic acid) is disclosed for producing pharmaceutical compositions suitable to be topically applied for treating dermatoses, such as ichthyosis and psoriasis.

4 Claims, No Drawings

THERAPEUTICAL METHOD FOR THE TREATMENT OF DERMATOSES USING O-ESTERS OF L-CARNITINE

The present invention relates to the use of O-esters of L-carnitine for producing pharmaceutical compositions containing such esters as active ingredients, suitable to be topically applied for the treatment of dermatoses. These esters have the formula (I)

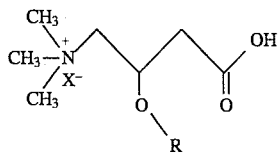

wherein

R is the acyl group of
(a) a saturated bicarboxylic acid, or
(b) an unsaturated monocarboxylic acid, and X− is the anion of a pharmacologically acceptable acid.

Specifically, the esters which are particularly preferred are those wherein acid (a) is selected from azelaic acid, sebacic acid, suberic acid and pimelic acid, and those wherein acid (b) is selected from arachidonic acid.

Encompassed by the esters to be used according to the present invention are also the inner salts of the compounds of the formula (I). In the inner salts the quaternary nitrogen atom will be salified by the carnitine carboxyl group or, possibly, when R is the acyl group of a bicarboxylic acid (a), by the free carboxyl group of the acid.

Pharmaceutically acceptable salts of the compound of formula (I) include, in addition to the inner salts, all pharmaceutically acceptable salts which are prepared by the addition of acid to L-carnitine, and which do not give rise to undesirable toxic or collateral effects. The formation of pharmaceutically acceptable acid addition salts is well known in pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

The esters of the formula (I) wherein the, acyl group is derived from the previously listed acids (a) and (b), are known compounds. Particularly:

the esters wherein the acyl group is derived from acids (a) are disclosed e.g. in U.S. Pat. No. 4,401,827 wherein their therapeutical utility for treating cardiac disturbances, hyperlipoedemias and hyperlipoproteinemic is also disclosed;

the esters wherein the acyl group is derived from acids (b) are disclosed e.g. in Biochem. Biophys. Acta 260, 515–526 (1972).

Both the U.S. patent and the aforesaid publication are incorporated by reference in the present specification. The dermatoses which are suitably treated with the compositions of the present invention are in particular ichthyosis, psoriasis and those dermatoses which are induced by a defective keratinization, such as dandruff, acne and palmar and plantar hyperkeratosis.

Ichthysosis is a dermatosis characterized by generalized dryness, harshness and scaling of the skin. It may occur hereditary disease present at birth, or as a metabolic disorder associated with hypothyroidism or with the intake of drugs (such as butyrophenols) inhibiting lipid synthesis, or as a paraneoplastic syndrome, manifestation of a tumor process involving internal organs.

Xeroderma, the mildest form of ichthyosis is neither congenital nor associated with systemic abnormalities.

It usually occurs on the lower legs of middle-aged or older patients, most often in cold weather and in patients who bathe frequently. There may be mild to moderate itching and an associated dermatitis due to detergents or other irritants.

The inherited ichthyoses, all characterized by excessive accumulation of scale on the skin surface, are classified according to clinical, genetic, and histologic criteria.

Known treatments of any form of ichthyosis comprise topically applying to the skin hydrating emollients. Furthermore, salicylic acid or vitamin A-containing ointments have been widely used.

A keratolytic agent particularly effective in removing the scale in ichthyosis vulgaris, lamellar ichthyosis and sex-linked ichthyosis contains 6% salicylic acid in a gel composed of propylene glicol, ethyl alcohol, hydroxypropylene cellulose and water.

Further known drugs for the treatment of this disorder include: 50% propylene glicol in water, hydrophilic petrolatum and water (in equal parts), and cold cream and an a-hydroxy acid (e.g. lactic and pyruvic acid) in various bases. In lamellar ichthyosis, 0.1% tretinoin (vitamin A acid; retinoic acid) cream has been utilized. None of these treatments has been found satisfactorily effective.

Hyperkeratosis is a thickening of the stratum corneum of the skin.

The treatment of choice is the topical application of drugs containing urea, propylene glicol or salicylic acid. Also in this case, none of the known treatment has proved to be satisfactorily effective.

It has now been found that the compounds of the present invention, when topically applied as solutions, lotions, creams or ointments containing from 0,01% to 20%, preferably from 1% to 15% and most preferably from 2 to 10% by weight of at least one of the foregoing compounds, are potently effective in achieving complete remission of ichthyotic conditions in humans and in healing psoriasis and those disorders brought about by an altered keratinization, such as dandruff, acne and palmar and plantar hyperkeratosis.

It has also been found that, if the solutions, creams or ointments of the invention are applied regularly on a daily basis, within about two to three weeks the effected skin areas will return to normal conditions. In order to prepare the compositions off this invention, at least one off the compounds of the formula (I) is preferably dissolved in water or ethanol initially. The solution prepared may be admixed in the conventional manner with commonly available ointment bases such as hydrophilic ointment (USP) or petrolatum (USP).

The water or ethanol used to dissolve the compounds according to this invention may range in concentration of from 1 to 30%, by volume, of the total composition.

The compounds of this invention may also be formulated in a solution or lotion form.

For instance, a compound of the formula (I) is dissolved directly in a mixture of water, ethanol and propylene glicol (40:40:20 by weight).

Some examples of the formulation are hereinbelow described:

Formulation 1:5% solution 5 grams of a compound of the formula (I) were dissolved in 5 mL of water and the resulting solution admixed with 40 mL of ethanol and 20 mL of propylene glicol. Sufficient water was added to make 100 mL of formulation.

Formulation 2:5% ointment 5 grams of a compound of the formula (I) were admixed with 95 grams of USP grade hydrophilic ointment, until an uniform consistency resulted.

What is claimed is:

1. A therapeutical method for treating ichthyosis, psoriasis, dandruff, acne and palmar and plantar hyperkeratosis which comprises topically applying to the skin of a patient in need thereof a dermatologically effective amount of a L-carnitine ester having the formula (I)

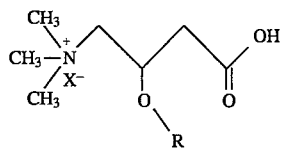

wherein

R is an acyl group of (a) a saturated bicarboxylic acid selected from the group consisting of azelaic, sebacic, suberic and pimelic acid, or
(b) an unsaturated monocarboxylic acid selected from the group consisting of linoleic, oleic and arachidonic acid; and X is the anion of a pharmacologically acceptable acid.

2. The method of claim 1, which comprises topically applying a pharmaceutical composition comprising from 0.01% to 20% by weight of an ester of formula (I) and a pharmacologically acceptable excipient.

3. The method of claim 2, which comprises topically applying a pharmaceutical composition comprising from 1% to 15% by weight of an ester of formula (I) and a pharmacologically acceptable excipient.

4. The method of claim 2, which comprises topically applying a pharmaceutical composition comprising from 2% to 10% by weight of an ester of formula (I) and a pharmacologically acceptable excipient.

* * * * *